(12) United States Patent
Horita

(10) Patent No.: US 7,651,870 B2
(45) Date of Patent: Jan. 26, 2010

(54) ANALYTE TREATING DEVICE

(75) Inventor: Takashi Horita, Osaka (JP)

(73) Assignee: Hitachi Maxell, Ltd., Ibaraki-shi, Osaka (JP)

( * ) Notice: Subject to any disclaimer, the term of this patent is extended or adjusted under 35 U.S.C. 154(b) by 923 days.

(21) Appl. No.: 11/104,596

(22) Filed: Apr. 13, 2005

(65) Prior Publication Data

US 2005/0250221 A1 Nov. 10, 2005

(30) Foreign Application Priority Data

Apr. 14, 2004 (JP) ............................ P2004-118726

(51) Int. Cl.
G01N 33/553 (2006.01)
G01N 33/00 (2006.01)
B03C 1/00 (2006.01)
B03C 1/18 (2006.01)
B01L 3/00 (2006.01)
G01N 21/00 (2006.01)
G01N 31/00 (2006.01)

(52) U.S. Cl. ........................... 436/526; 422/61; 422/63; 422/99; 422/102; 422/104; 209/8; 209/38; 209/39; 209/40

(58) Field of Classification Search ................ 436/526; 422/61, 63, 99, 100, 102, 104; 209/8, 38–40
See application file for complete search history.

(56) References Cited

U.S. PATENT DOCUMENTS 5,238,810 A * 8/1993 Fujiwara et al. ................ 435/5

| | | | |
|---|---|---|---|
| 6,126,765 A | 10/2000 | Ohman | |
| 6,620,478 B1 | 9/2003 | Ohman | |
| 6,875,402 B2 | 4/2005 | Hirota et al. | |
| 2001/0035350 A1 | 11/2001 | Seki et al. | |
| 2002/0122748 A1 | 9/2002 | Hirota et al. | |

FOREIGN PATENT DOCUMENTS

| JP | 9-502795 A | 3/1997 |
| JP | 2001-281233 A | 10/2001 |
| JP | 2002-159285 A | 6/2002 |
| JP | 2002-204945 A | 7/2002 |
| JP | 2003-279537 A | 10/2003 |

* cited by examiner

*Primary Examiner*—Jill Warden
*Assistant Examiner*—Dean Kwak
(74) *Attorney, Agent, or Firm*—Birch, Stewart, Kolasch & Birch, LLP

(57) ABSTRACT

A device for treating an analyte using magnetic beads is provided wherein the surfaces of the magnetic beads are effectively available as a whole. The device comprises a housing having a channel therein, through which channel the analyte is moved; a pair of electromagnets which are oppositely arranged in such a manner that the channel is interposed therebetween; a moving means for moving the pair of electromagnets along the channel while the electromagnets are facing the channel; and a controlling means for controlling magnetic forces generated by the electromagnets. The device is characterized in that the magnetic forces of the electromagnets are alternately generated with time. This will cause the magnetic beads to collide successively with the inner surface of the channel, which in turn gives a more efficient dispersion of the magnetic beads even if they are clustered or agglutinated to each other.

6 Claims, 6 Drawing Sheets

ANALYTE TREATING DEVICE

CROSS REFERENCE TO RELATED PATENT APPLICATION

The present application claims the right of priority of Japanese Patent Application No. 2004-118726 (filed Apr. 14, 2004, the title of the invention: "REACTOR"), the disclosure of which is incorporated herein by reference in its entirety.

FIELD OF THE INVENTION

The present invention relates to a device for treating analyte(s) with the use of magnetic beads. Therefore, the device of the present invention is used for analysis of the gene structure or gene sequence of an analyte in a medical field.

BACKGROUND OF THE INVENTION

Gene information such as the gene structure or gene sequence of the human varies between individuals. The attention is currently focused on Taylor-made Medical Technology which allocates care appropriately for individuals according to their differences. The gene information is composed of the base sequence of DNA (i.e. deoxyribonucleic acid). The base sequence of DNA varies between individuals. For example, there generally exists SNP (single nucleotide polymorphisms) in which variations occur at a rate of one in every 1000 bases. The possibility of coming down with some illnesses, and also the effect of the drug medicines are different depending on a SNP type. Accordingly, on the basis of the result of the SNP examination, it is possible to effectively allocate care by determining a type of the drug medicines and/or an amount thereof. To be more precise as to the SNP examination, a SNP type is identified by obtaining a sample such as human blood or human cell to isolate DNA thereof, followed by analyzing a genome sequence of the gene parts necessary for the remedy.

In order to analyze the gene structure or gene sequence and the like, various sorts of small analyte treating devices (e.g. devices used as the reactor) have been developed so far (see Japanese Patent Kokai Publication No. 2001-281233 (paragraphs 0027 and 0028 as well as FIG. 1), Japanese Patent Kokai Publication No. 2002-159285 (paragraphs 0015 to 0017 and FIG. 1), Japanese Patent Kokai Publication No. 2002-204945 (paragraph 0040 and FIG. 1), Japanese Patent Kokai Publication No. 2003-279537 (paragraph 0016 and FIG. 1), and Japanese Patent Kokai Publication No. 9-502795 (lower section of page 4 and FIG. 2), for example).

FIG. 7 illustrates a conventional housing for use in a small device for treating an analyte. As shown in FIG. 7, the housing 3, which is generally in a slab shape or a flat-plate shape, is composed of a body 11 and a lid member 12. The body 11 is provided with a plurality of parallel channels 20 (e.g. two channels in the case of the body shown in FIG. 7). The lid member 12 is provided with small pores 13 arranged at such a position that they face both ends of each channel 20. Not a sample containing analyte(s), but also a reagent is charged into the channel 20 through one of the small pores 13. Subsequently, the analyte(s) are moved along the channel 20 while reacting with the reagent. Finally, the analyte(s) are recovered or collected from the other small pore 13 after the reaction is completed. Incidentally, a housing in another form is also available wherein a plurality of the above-mentioned housings are stacked to each other.

FIG. 8 illustrates further another housing in another form. A body 11 of a housing 3 is provided with a comb-like channel. That is to say, there is provided a main channel 1, and a plurality of sub-channels 2 that diverge from the main channel 1. As for a lid member 12 of the housing 3, as shown in FIG. 8, there is provided small pores 13 arranged at such a position that they face both ends of the main channel 1 and one end of each sub-channel 2. In treating the analyte(s), a reagent is charged into each sub-channel 2 through the small pore 13 facing one end of each sub-channel 2. This means that it is possible to house different kinds of reagents in the respective sub-channels 2. Consequently, a sample containing analyte(s) is charged into the sub-channel 2 through the small pore 13 facing one end of the main channel 1. After that, the analyte(s) are moved successively through respective sub-channels 2 via the main channel 1, so that the analyte(s) are successively reacted with different kinds of reagents. In the movement of the analyte(s), it is also possible to carry out a washing process and the like.

As a means for moving the analyte(s) along the channel of the housing, a combination of magnetic beads having affinity for the analyte(s) and electromagnet is employed. Hereinafter, this will be described by taking the housing 3 shown in FIGS. 8 and 9 as an example. First, as shown in FIG. 9, an electromagnet 21 is arranged at the outer side of the housing 3, and also a lot of magnetic beads (not shown) having affinity for analyte(s) are charged into the sub-channel 2 of the housing 3. Eventually, this causes the analyte(s) to bind to the magnetic beads. Subsequently, the electromagnet 21 is moved along the sub-channel 2 (or main channel 1) under such a condition that the magnetic beads are allowed to be attracted by the magnetic force of the moving electromagnet 21.

SUMMARY OF THE INVENTION

In the case where the analyte(s) are treated with the use of a lot of the magnetic beads, there is a possibility that the magnetic beads are clustered or agglutinated to each other due to the magnetic force of their own, as shown in FIG. 10. As a result, a total surface area of the magnetic beads, which area is available for biding of the analyte(s) 16, will decrease. This will lead to a decrease in the amount of the analyte(s) 16 bound to the magnetic beads.

Therefore, an object of the present invention is to provide a device for treating analyte(s) (which is hereinafter referred to also as "analyte treating device"), which enables a decrease in the clustering or agglutination of the magnetic beads.

In order to achieve the object, the present invention provides a device for treating an analyte, comprising:

a housing having a channel therein, through which channel the analyte is moved;

a pair of electromagnets (or electromagnet members) which are oppositely arranged in such a manner that the channel is interposed therebetween;

a moving means for moving the pair of electromagnets along the channel while the electromagnets are facing the channel; and a controlling means for controlling magnetic forces generated by the electromagnets;

wherein the magnetic forces of the electromagnets are alternately generated with time.

Additionally, the present invention provides a method for treating an analyte by moving the analyte through a channel, comprising:

moving a pair of electromagnets along the channel while the electromagnets are facing the channel, which electromagnets are arranged outside the channel that contains the analyte and magnetic beads having affinity for the analyte; and concurrently generating magnetic forces of the electromagnets alternately with time.

The analyte treating device of the present invention is used together with a lot of the magnetic beads having affinity for the analyte(s). Accordingly, the present invention also provides an assembly for treating an analyte (which is hereinafter referred to also as "analyte treating assembly") or a kit for treating an analyte (which is hereinafter referred to also as "analyte treating kit"), both of which comprise magnetic beads as well as the analyte treating device. Incidentally, the phrase "analyte treating assembly" is directed to an embodiment wherein the magnetic beads are preliminarily housed in the channel of the analyte treating device, whereas the phrase "analyte treating kit" is directed to an embodiment wherein the magnetic beads are not preliminarily housed in the channel of the analyte treating device.

In order to analyze the gene structure or gene sequence of the analyte(s), reaction(s) between analyte(s) and reagent(s) may be carried out. In this case, the analyte treating device of the present invention is viewed as a "reactor".

Both of the phrases "treating an analyte" and "analyte treating" herein mean a commonly used treatment for analyzing the gene structure of gene sequence and the like. That is to say, these phrases mean that the analyte(s) or specimen(s) bound to magnetic bead(s) are contacted with a fluid such as a reagent. The examples corresponding to the phrases "treating an analyte" and "analyte treating" include a reaction between analyte(s) and reagent(s) due to a contact therebetween, or a washing treatment due to a contact between a fluid and magnetic beads after a reaction therebetween is completed.

The analyte treating device is characterized in that magnetic forces of a pair of electromagnets are alternately generated for exercising an effect on the magnetic beads. The magnetic beads housed in the channel will be attracted toward the electromagnet that generates the magnetic force. As a result, the magnetic beads will collide with an inner surface of the channel (i.e. housing). Therefore, the impact of the collision will cause the clustered or agglutinated beads to disperse. This will lead to an increase in a total surface area of the magnetic beads, which area is available for binding of the analyte(s).

Figure 1:
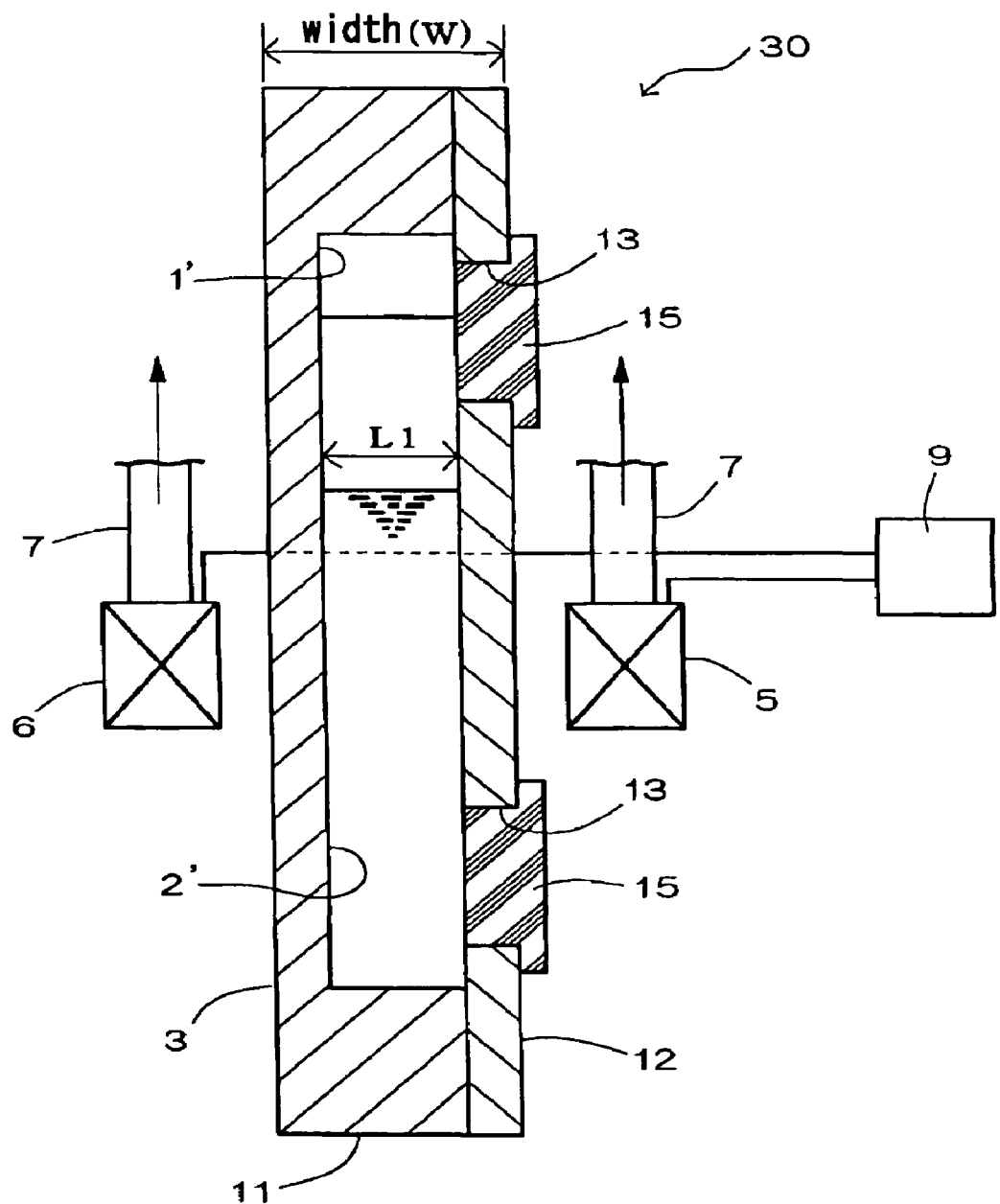
FIG. 1 is a sectional side view of an analyte treating device of the present invention taken along the line A-A' shown in FIG. 2.

In the drawing, the reference numbers correspond to the following elements:

1 . . . main channel, 1' . . . first channel, 2 . . . sub-channel, 2' . . . second channel, 3 . . . housing, 5 . . . first electromagnet, 6 . . . second electromagnet, 7 . . . moving means, 9 . . . controlling means, 10. . . magnetic bead(s), 11 . . . body of housing, 12 . . . lid member of housing, 13 . . . small pore, 15 . . . plug, 16 . . . analyte(s), 20 . . . channel, 21 . . . electromagnet, and 30 . . . analyte treating device.

DETAILED DESCRIPTION OF THE PREFERRED EMBODIMENTS

Hereinafter, an analyte treating device, an analyte treating assembly and an analyte treating kit will be described in more detail with reference to the attached figures. The difference between the analyte treating device and the analyte treating assembly or kit is whether or not the magnetic beads are preliminarily provided, thus, such difference is considered marginal. Accordingly, the analyte treating device will be mainly described hereinafter.

Figure 2:
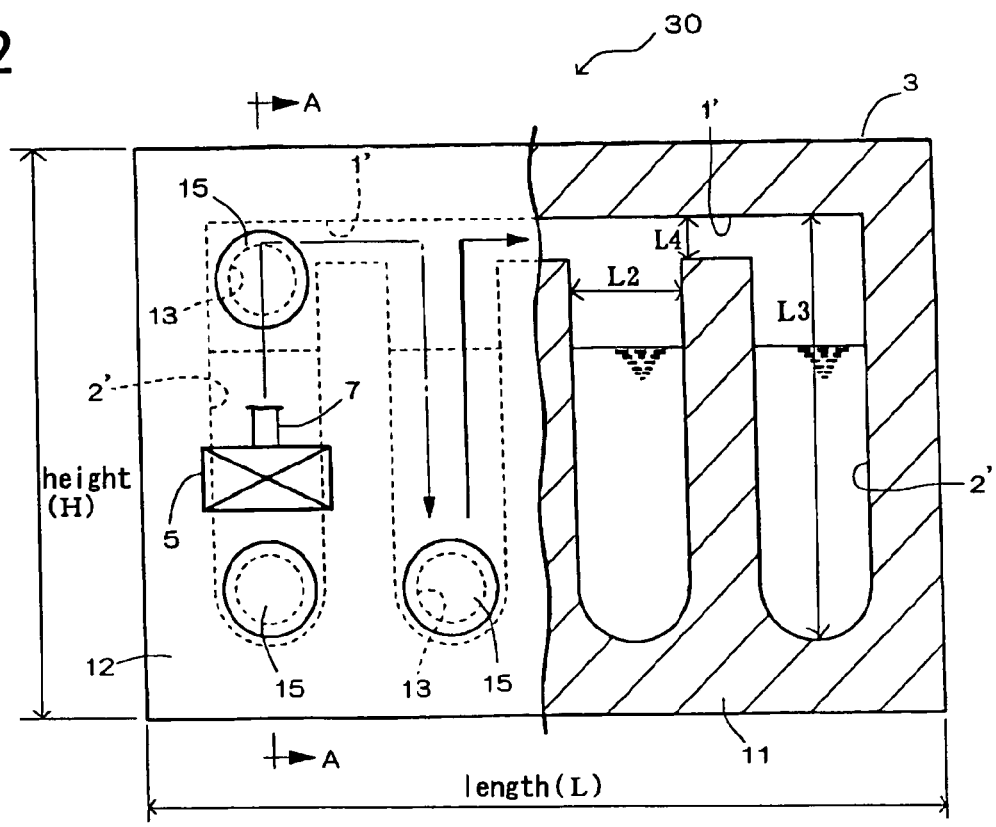
FIG. 2 is a front view of an analyte treating device wherein a part of it is illustrated in cross-section.

The housing used in the analyte treating device of the present invention is provided with a hollow portion therein, which portion not only serves to house analyte(s) (or a sample containing the analyte(s)) and/or a reagent and the like, but also serves as a channel of the analyte(s). Therefore, as shown in FIG. 1, it is preferred that the housing is composed of a lid member 12 and a body 11 having channels formed therein. The housing is preferably in a slab shape or a flat-plate shape. Therefore, as shown in FIGS. 1 and 2, it is preferred that the housing is in the range from 0.3 to 10 mm in width (W) (see FIG. 1), from 2 to 300 mm in length (L) (see FIG. 2), and from 2 to 300 mm in height (H) (see FIG. 2). It is more preferred that the housing is in the range from 0.5 to 5 mm in width (W), from 5 to 150 mm in length (L), and from 5 to 150 mm in height (H).

Figure 8:
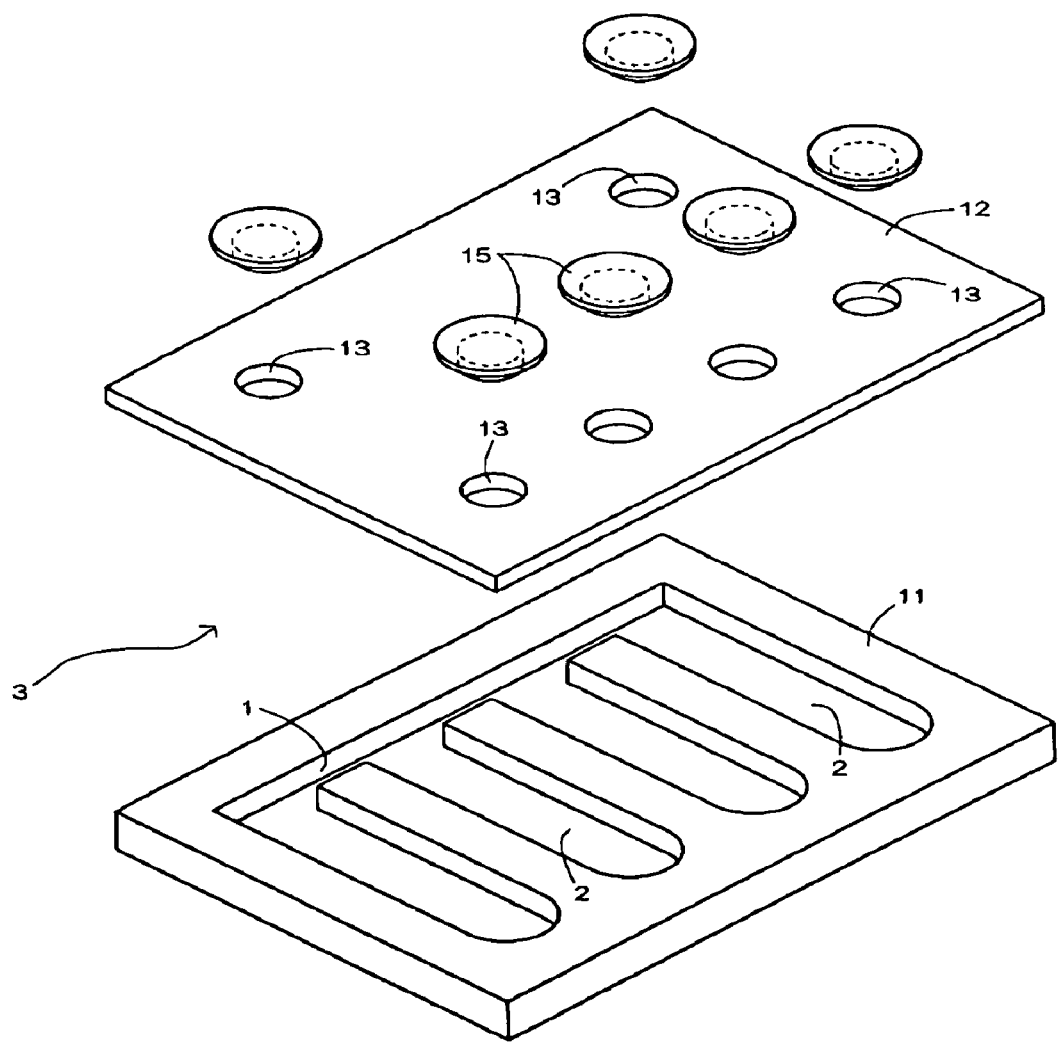
FIG. 8 is a perspective view illustrating another housing of a commonly used analyte treating device.
Figure 9:
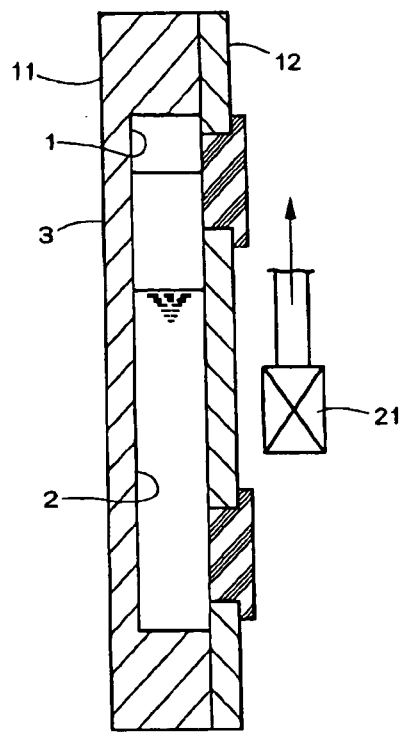
FIG. 9 is a sectional side view of a commonly used analyte treating device.
Figure 10:
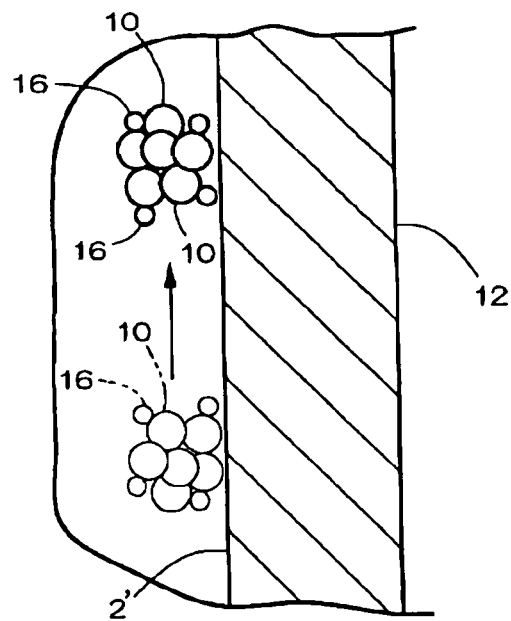
FIG. 10 is a sectional view illustrating movements of magnetic beads in the case of a commonly used analyte treating device.

The hollow portion of the housing may be in any shape or form so long as it has a space that houses a fluid such as a sample containing analyte(s) and/or a reagent as well as allows analyte(s) to move therethrough. As shown in FIG. 2, it is preferred that the hollow portion is in a comb-like shape as a whole. That is to say, it is preferred that a channel of the housing is composed of a first channel 1' and a plurality of second channels 2' that diverge from the first channel 1'. The first channel 1' corresponds to a main channel 1 of the housing 3 shown in FIG. 8. The second channels 2' correspond to sub-channels 2 of the housing 3 shown in FIG. 8. To be more precise, it is preferred that the first channel 1' is arranged in the direction perpendicular to the extending direction of the second channels 2' in such a manner that the first channel 1' is communicated with one end of each second channel 2'. In this case, the first channel 1' and the second channel 2' may be respectively in a rectangular shape or a cylindrical shape, for example. The end of the second channel may be in a semicircular shape (see FIG. 2). For example, in the case where the channel of the housing is in a comb-like shape as shown in FIGS. 1 and 2, it is preferred that the length corresponding to L1 (see FIG. 1) ranges from 0.1 to 8 mm, the length corresponding to L2 (see FIG. 2) ranges from 0.1 to 20 mm, the length corresponding to L3 (see FIG. 2) ranges from 1.5 to 280 mm, and the length corresponding to L4 (see FIG. 2) ranges from 0.1 to 8 mm. It is more preferred that the length corresponding to L1 ranges from 0.3 to 4 mm, the length corresponding to L2 ranges from 0.3 to 10 mm, the length corresponding to L3 ranges from 4 to 140 mm, and the length corresponding to L4 ranges from 0.3 to 4 mm.

The lid member 12 of the housing is provided with small pores 13 arranged at such a position that they face the end of the first channel 1' and each second channel 2'. This means that it is possible to charge a fluid such as analyte(s) (or sample containing analyte(s)) and/or a reagent into the housing through the small pore 13, and that it is also possible to recover or collect the treated analyte(s) therethrough. After charging a fluid such as the analyte(s) (or sample containing analyte(s)) and/or the reagent into the housing, the small pore 13 is covered with a plug (or a cap) 15 made of a synthetic rubber. It is preferred that the body 11 of the housing and the lid member 12 thereof are bonded to each other by applying of an adhesive and/or a two-sided tape therebetween.

The body 11 of the housing and the lid member 12 thereof may be made of any material so long as they can withstand a collision of the magnetic beads. For example, both of the body and the lid member may be made of a material selected from the group consisting of a resin, a metal, a ceramic and a complex thereof.

A pair of electromagnets used in the analyte treating device of the present invention are arranged at the outer side of a channel (i.e. first channel or second channel) of the housing in such a manner that the channel is interposed therebetween. To be more precise, as shown in FIG. 1, a first electromagnet 5 and a second electromagnet 6 are oppositely arranged in such a manner that the first electromagnet 5 is positioned near the lid member (12) and the second electromagnet 6 is positioned near the housing body (11). It is preferred that a width dimension of each of the first and second electromagnets is slightly larger than that of the second channel (i.e. the length L2 shown in FIG. 2).

Any kind of electromagnet may be used so long as it generates a magnetic force enabling its attraction for the magnetic beads housed in the channel. The magnetic surface flux density as to the electromagnet is preferably in the range from 20 to 2000 mT, and more preferably in the range from 50 to 1000 mT.

It is possible to move a pair of electromagnets with the aid of a moving means. To be more precise, the moving means 7 is connected to a pair of electromagnets 5, 6 as shown in FIG. 1. The moving means 7 allows the first electromagnet 5 and the second electromagnet 6 to move along the first or second channels above the outer surface of the housing while both of the two electromagnets are facing the first or second channels. The moving velocity of a pair of electromagnets is preferably in the range from 0.1 to 100 cm/second, and more preferably in the rage from 0.5 to 50 cm/second.

Figure 4:
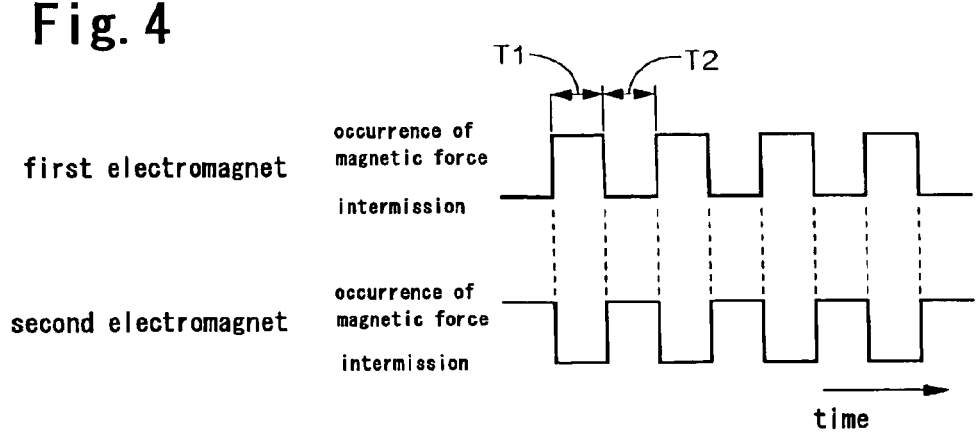
FIG. 4 is a timing chart illustrating an occurrence of magnetic forces concerning a first electromagnet and a second electromagnet.

An electric current, which is supplied from a controlling means 9 to a pair of electromagnets, causes the magnetic force to generate in each of the two electromagnets. The analyte treating device of the present invention is characterized in that a magnetic force of the first electromagnet 5 and a magnetic force of the second electromagnet 6 are alternately generated to each other as time advances. As shown in FIG. 4, by means of the controlling means 9, an electric current applied to the second electromagnet is intermitted so as not to generate a magnetic force of the second electromagnet during a time period T1 when an electric current is being applied to the first electromagnet so as to generate a magnetic force of the first electromagnet. In a similar way, an electric current applied to the first electromagnet is intermitted so as not to generate a magnetic force of the first electromagnet during a time period T2 when an electric current is being applied to the second electromagnet so as to generate a magnetic force of the second electromagnet. The time periods T1 and T2 are preferably in the rage from 0.2 to 30 seconds respectively, and more preferably in the range from 0.3 to 10 seconds respectively.

Figure 3:
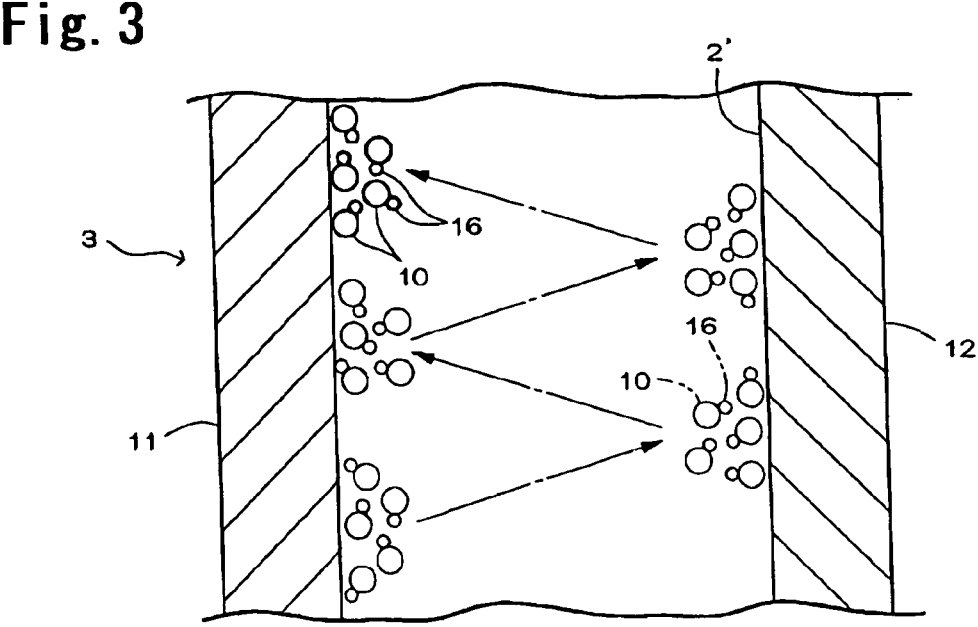
FIG. 3 is a sectional side view illustrating a movement of magnetic beads that was housed in a channel of an analyte treating device of the present invention.

In the case where the magnetic force of the first electromagnet 5 and the magnetic force of the second electromagnet 6 are alternately generated to each other as time advances, the magnetic beads housed in the device will be alternately attracted toward the first electromagnet and the second electromagnet. As a result, as shown in FIG. 3, the magnetic beads will repeatedly collide with an inner surface of the channel. Therefore, the impact of the collision will cause the clustered or agglutinated beads to disperse. This will lead to an increase in a total surface area of the magnetic beads, which area is available for binding of the analyte(s).

The magnetic bead used along with the analyte treating device of the present invention is preferably made of a magnetic material selected from the group consisting of metals (e.g. ferrum, cobalt and nickel), an alloy thereof and an oxide thereof. It is preferred that the magnetic bead is in a spherical shape and also is approximately in the range from 1 to 10 μm in diameter thereof. It is required that the surface of the magnetic bead is coated with a material having affinity for an analyte. The reason for this is that the analyte 16 can bind to (or be adsorbed by) the magnetic bead 10 through the intervention of such material having affinity for the analyte (see FIG. 3). It is preferred that the material having affinity is selected from the group consisting of a silica, a metal, a compound or polymer having an adsorptive functional moiety, and biological materials such as a protein, a saccharide, a nucleic acid and an apatite. For example, in the case where the analyte is DNA, the silica is used as the material having affinity therefor.

In the next place, a manipulation and a working of the analyte treating device (including analyte treating kit and analyte treating assembly) of the present invention will be described hereinafter.

First, through the small pore 13, a lot of magnetic beads are charged into the second channel 2' positioned at the left side of the housing as shown in FIG. 2. In this connection, in the case where the analyte treating assembly is used, there is no need to charge magnetic beads into the second channel 2' since such magnetic beads are preliminarily housed therein. In the respective second channels 2' of the analyte treating device 30, various kinds of fluids (e.g. reagent and/or washing fluid) have been already charged. Examples of such fluids may include water, an organic solvent, a buffer, a surfactant, various biological materials each alone and any mixture thereof. Subsequently, a sample containing analyte(s) is charged into the second channel 2' through the small pore 13 facing the left-sided end of the first channel 1'. It is preferred that the sample is in a liquid state. Examples of the analyte may include a bodily fluid (e.g. blood, urine and saliva), a biological tissue fragment, microorganisms and various kinds of compounds for which a functional study or a screening is to be carried out. As both of the magnetic beads and the analyte(s) are charged into the second channel 2', the analyte(s) bind to the surfaces of the magnetic beads due to the bead's affinity for the analyte(s). At this moment, as shown in FIG. 2, the first and second electromagnets are put in a standby mode. That is to say, the first and second electromagnets are arranged at such a position that both of them face the lower end of the left-sided second channel 2' of the analyte treating device 30 (in FIG. 2, only the first electromagnet can be seen). Subsequently, the magnetic forces of the first and second electromagnets are alternately generated with the aid of a controlling means. This will cause the magnetic beads to be attracted toward the electromagnet that generates the magnetic force. Therefore, by moving the first and second electromagnets upward along the second channel 2 with the aid of the moving means 7, not only the magnetic beads but also the analyte(s) are also moved upward along the second channel 2'.

To sum it up, the magnetic forces of the first and second electromagnets are alternately generated with the aid of a controlling means while the first and second electromagnets are moving upward along the second channel. As a result, as shown in FIG. 3, the magnetic beads 10 move upward while colliding with the inner surface of the second channel 2'. Accordingly, the impact of the collision will cause the clustered or agglutinated magnetic beads to disperse. To be more precise, when the magnetic force of the first electromagnet is generated, the magnetic beads are attracted toward the lid member 12 and thereafter they collide with the inner surface of the lid member 12. On the contrary, when a magnetic force of the second electromagnet is generated, the magnetic beads are attracted toward the housing body 11 and thereafter they collide with the inner surface of the housing body 11. The disperse of the clustered or agglutinated magnetic beads will lead to an increase in a total surface area of the magnetic beads, which area is available for biding of the analyte(s). Therefore, more analytes can bind to the magnetic beads.

Subsequently, as shown in FIG. 2, the first and second electromagnets are sequentially moved in a left-to-right direction in such a manner that they face the second channels 2' through the first channel. This will cause the analyte(s) bound to the magnetic beads to move sequentially in a left-to-right direction through the respective second channels 2' of the analyte treating device. As a result, the analyte(s) are sequentially reacted with various kinds of reagents housed in the respective second channels 2'. Finally, the reacted analytes are to be recovered (or collected) through the small pore 13 facing the right-sided second channel. The above-mentioned processes will result in an analysis of the gene structure or gene sequence of the analyte(s).

Incidentally, in the case when the first and second electromagnets are moved along the first channel 1', it could be possible to generate only one magnetic force by one of the two electromagnets.

Hereinabove, the embodiments of the analyte treating device, the analyte treating assembly and the analyte treating kit have been described according to the present invention. However, the description of such embodiments is for purposes of illustration and not limitation, and so it's a matter of course that such embodiments may be diversely modified.

Figure 5:
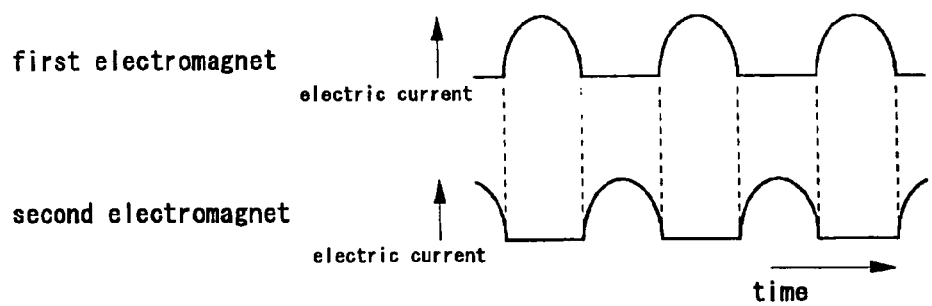
FIG. 5 is a timing chart illustrating an occurrence of magnetic forces concerning a first electromagnet and a second electromagnet wherein an electric current applied to each of them is in a semi-sinusoidal form.

In a preferred embodiment of the invention, as shown in FIG. 5, an electric current applied to each of the first and second electromagnets may be in a semi-sinusoidal form or profile. In this case, it is preferred that, with the aid of the controlling means, an alternating electrical current having a predetermined frequency (e.g. frequency obtained from a commercially available power supply) is half-wave rectified, and thereafter the half-wave rectified electrical current is applied to the respective first and second electromagnets in such a manner that a phase lag thereof is provided. In the case of the semi-sinusoidal electric current, there are some advantages in that a frequency obtained from a commercially available power supply can be used, and that a circuit for generating such semi-sinusoidal electric current can be simplified.

Figure 6:
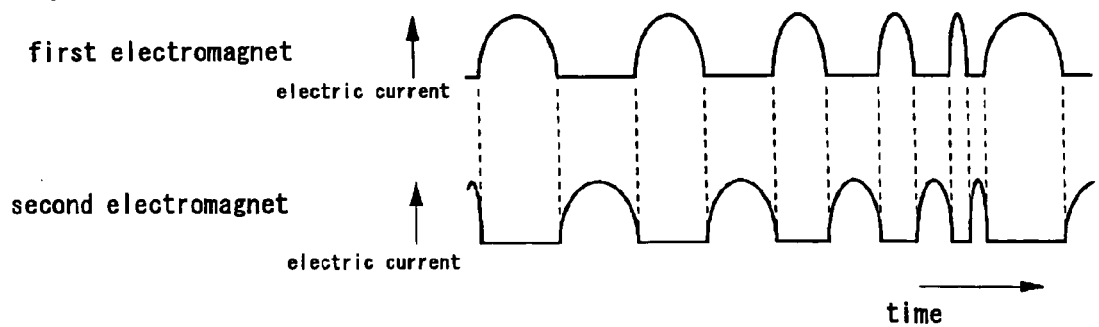
FIG. 6 is a timing chart illustrating an occurrence of magnetic forces concerning a first electromagnet and a second electromagnet wherein an electric current applied to each of them is in a semi-sinusoidal form and also is frequency-modulated.
Figure 7:
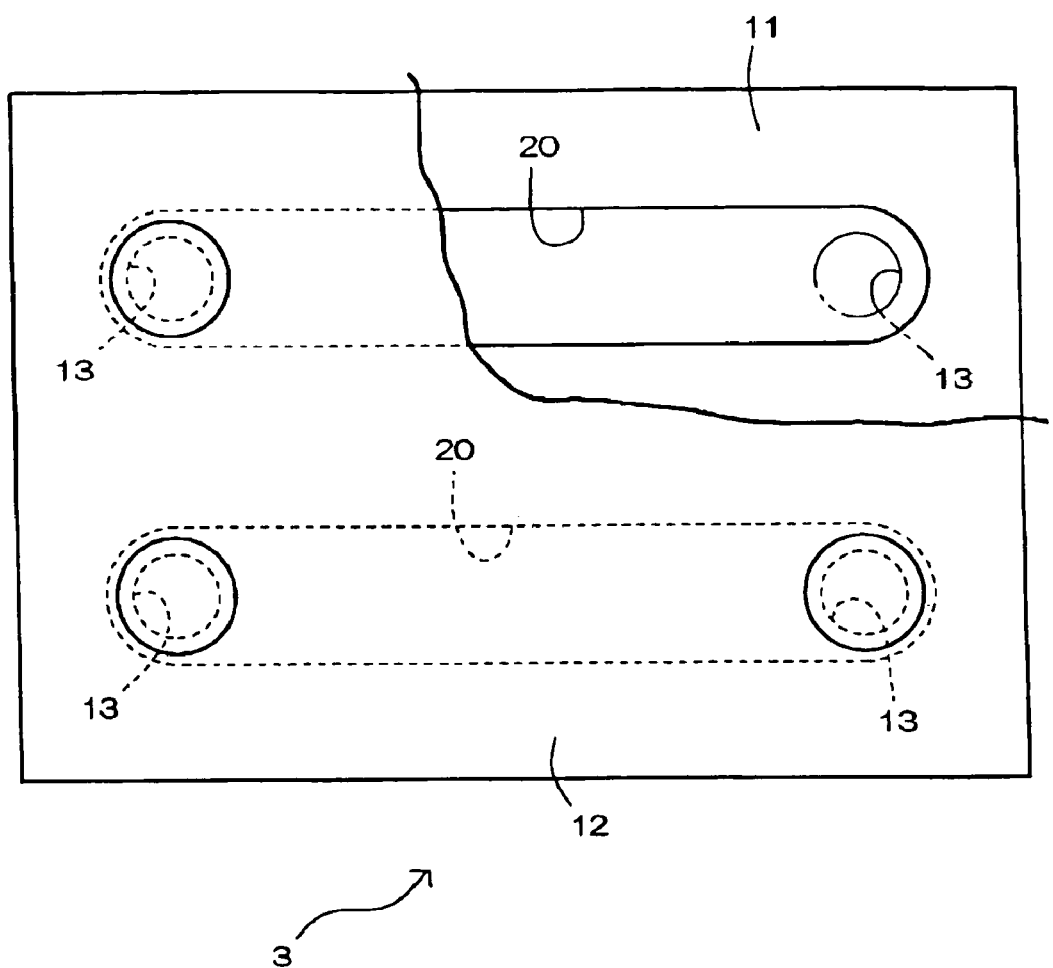
FIG. 7 is a front view of a housing of a commonly used analyte treating device.

In another preferred embodiment of the invention, as shown in FIG. 6, an electric current applied to each of the first and second electromagnets may be in a semi-sinusoidal form wherein the semi-sinusoidal electric current is frequency-modulated. In this case, it is preferred that, with the aid of the controlling means, an alternating electrical current having a predetermined frequency is frequency-modulated and then is half-wave rectified, and thereafter the half-wave rectified electrical current is applied to the respective first and second electromagnets in such a manner that a phase lag thereof is provided. In the case of the frequency-modulated electric current with a semi-sinusoidal form, an impact of the collision between magnetic beads and the inner surface of the channel is. successively changed, which in turn leads to a more efficient dispersion of the magnetic beads.

Incidentally, so long as the magnetic forces of the first and second electromagnets are alternately generated to each other, an electric current applied to each of the first and second electromagnets may be in any wave-form or may have any frequency. Likewise, an electric current applied to each of the first and second electromagnets may be modulated as appropriate. Therefore, an electric current applied to each of the first and second electromagnets may be in a semi-sinusoidal form wherein the semi-sinusoidal electric current is amplitude-modulated, for example.

Furthermore, it is not necessarily the case that the number of the electromagnet used for the analyte treating device of the present invention is "two". That is to say, more than two (e.g. three or four) electromagnets may be used as desired. In this case, the respective electromagnets are controlled to generate their magnetic forces alternately with time.

What is claimed is:

1. A device for treating an analyte, comprising:
   a housing having a channel therein having a channel width of 0.1 to 8 mm, through which channel the analyte is moved;
   a pair of electromagnets which are oppositely arranged in such a manner that the channel is interposed therebetween;
   a moving means for moving the pair of electromagnets along the channel while the electromagnets are facing the channel; and
   a controlling means for controlling a power source applied to electromagnets;
   wherein magnetic forces of the electromagnets are alternately generated with time, in order to cause repeated collisions of clustered or agglutinated beads against an inner surface of the channel; and
   wherein said controlling means for controlling the power source applied to electromagnets comprises means to provide an electrical current having a phase lag between said electromagnets.

2. The device for treating an analyte according to claim 1, wherein said controlling means controls electric currents alternately applied to said electromagnets; and
   each of the electric currents is in a semi-sinusoidal form.

3. The device for treating the analyte according to claim 2, wherein each of the semi-sinusoidal electric currents is frequency-modulated.

4. The device for treating the analyte according to claim 2, wherein each of the semi-sinusoidal electric currents is amplitude-modulated.

5. A kit for treating an analyte, comprising:
   said device for treating the analyte according to claim 1; and
   magnetic beads to be used by housing them in said channel of the device, which beads have affinity for the analyte.

6. A method for treating an analyte by moving the analyte through a channel having a channel width of 0.1 to 8 mm, comprising:

moving a pair of electromagnets along the channel while the electromagnets are facing the channel, which electromagnets are arranged outside the channel that contains the analyte and magnetic beads having affinity for the analyte; and concurrently generating magnetic forces of the electromagnets alternately with time through a controlling means for controlling a power source applied to the electromagnets that comprises means to provide an electrical current having a phase lag between said electromagnets, and causing repeated collisions of clustered or agglutinated beads against an inner surface of the channel.

* * * * *